United States Patent
Chu et al.

(10) Patent No.: US 6,949,518 B1
(45) Date of Patent: Sep. 27, 2005

(54) METHODS FOR TREATING MACULAR DEGENERATION WITH TOPIRAMATE

(76) Inventors: Pao-Hsien Chu, 5216 Quaker Hill La., San Diego, CA (US) 92130; Hosheng Tu, 15 Riez, Newport Beach, CA (US) 92657

( * ) Notice: Subject to any disclaimer, the term of this patent is extended or adjusted under 35 U.S.C. 154(b) by 33 days.

(21) Appl. No.: 10/868,731

(22) Filed: Jun. 15, 2004

Related U.S. Application Data

(60) Provisional application No. 60/482,585, filed on Jun. 25, 2003.

(51) Int. Cl.[7] ............................................. A61K 31/70
(52) U.S. Cl. ....................... 514/23; 514/236.2; 514/912
(58) Field of Search .............................. 514/23, 236.2, 514/912, 913

(56) References Cited

U.S. PATENT DOCUMENTS

| | | | |
|---|---|---|---|
| 4,599,353 A | 7/1986 | Bito | |
| 5,153,192 A | 10/1992 | Dean et al. | |
| 5,238,961 A | 8/1993 | Woodward et al. | |
| 5,688,770 A * | 11/1997 | Watkins ...................... | 514/16 |
| 5,935,933 A | 8/1999 | Shank et al. | |
| 6,071,537 A | 6/2000 | Shank | |
| 6,201,010 B1 | 3/2001 | Cottrell | |
| 6,319,903 B1 | 11/2001 | Carrazana et al. | |
| 6,362,220 B1 | 3/2002 | Cottrell | |
| 6,559,293 B1 * | 5/2003 | Almarsson et al. ........ | 536/18.7 |
| 6,696,091 B2 | 2/2004 | Thakur et al. | |
| 6,699,840 B2 | 3/2004 | Almarsson et al. | |

OTHER PUBLICATIONS

C Laino "Topiramate Relieves Peripheral Neuropathy, Improves Metabolic Syndrome" Medscape Medical News 2003.

"Topiramate Effective in Preventing Migranes", Reuters Health Information 2004.

* cited by examiner

*Primary Examiner*—Zohreh Fay

(57) ABSTRACT

A method for treating macular degeneration and/or treating optic nerve degeneration of a patient comprises administering topiramate with a dosage pharmaceutically effective to suppress degeneration or induce growth of new optic nerve fibers over a sustained period.

15 Claims, No Drawings

METHODS FOR TREATING MACULAR DEGENERATION WITH TOPIRAMATE

CROSS-REFERENCE TO RELATED APPLICATIONS

The application claims priority benefits of provisional application Ser. No. 60/482,585, filed Jun. 25, 2003, entire contents of which are incorporated herein by reference.

FIELD OF THE INVENTION

The present invention generally relates to a new class of pharmaceuticals for treating macular degeneration and optic neuropathy. More particularly, the present invention relates to pharmaceutical agents that effectively induce the growth of new optic nerve fibers and/or reverse macular or optic nerve degeneration.

BACKGROUND OF THE INVENTION

There are two types of age-related macular degeneration (AMD): the dry (atrophic) form and the wet (exudative) form. The dry form of AMD affects about 90 percent of AMD patients and usually begins with the formation of tiny yellow deposits called drusen in the macula. Drusen usually do not cause serious loss of vision, but can cause distortion of vision. However, for reasons that are not yet understood, sometimes drusen will cause the macula to thin and break down, slowly leading to vision loss. The wet form of AMD occurs in about 10 percent of AMD patients. It is caused by the growth of abnormal blood vessels beneath the macula that can leak fluid and blood (i.e. exudate). The wet form of AMD typically causes significant vision problems in the affected eye and can progress very rapidly, causing permanent central vision loss. The exact cause of AMD is not known. AMD may be hereditary. Macular degeneration may never get better on its own.

Michael Schwartz (of the Weizmann Institute's Neurobiology Department) reports that capoxone may slow, or possibly stop the loss of eyesight in people with chronic glaucoma. Dr Schwartz's studies have shown that immunization with capoxone shields the optic nerve from the toxic effects of the neurotransmitter glutamate, which is released in increasing concentrations as the optic nerve degenerates. However, capoxone does not induce or stimulate the growth of new optic nerve fibers.

For the first time, researchers (a review article by Gary D. Vogin, MD in Medscape Medical News 2003. © 2003 Medscape) report that a pharmacologic intervention may effectively target the underlying abnormalities that lead to the development of type 2 diabetes. In a small pilot study in 11 patients with type 2 diabetes at an average age of 59 years (reported by Aaron I. Vinik, MD, PhD, director of the Strelitz Diabetes Research Institutes at Eastern Virginia Medical School in Norfolk, Va. at the American Diabetes Association 63rd Scientific Sessions, 2003), the anticonvulsant topiramate appeared to induce the growth of new nerve fibers and relieve symptoms of peripheral neuropathy while also improving components of metabolic syndrome. The patients were administered 25 mg/day, titrated over 42 days to the maximum tolerated dose or 100 mg/day. The patients received the anticonvulsant for 84 more days. By the end of trial, dendrite length and peroneal nerve amplitude had increased, and total neuropathy scores had decreased from 14 to 11.8. It suggests that intra-epidermal nerve fibers actually grew back and the nerve repairs itself. This provides the first opportunity to change the underlying biology of the disease as opposed to treating its symptoms. The above finding was presented at ADA 63rd Scientific Sessions: Abstract 66, presented Jun. 13, 2003, poster 1702, presented Jun. 14, 2003, entire contents of which are incorporated herein by reference.

U.S. Pat. No. 6,699,840, entire contents of which are incorporated herein by reference, discloses a controlled-release form of topiramate sodium trihydrate comprising topiramate sodium trihydrate and a means for controlled-release of the topiramate sodium trihydrate as a treatment method for symptoms.

U.S. Pat. No. 6,696,091, entire contents of which are incorporated herein by reference, discloses a pharmaceutical composition of topiramate as an anticonvulsant which is useful for treating epilepsy. More specifically, the invention provides a solid dosage formulation of topiramate intended primarily for use by pediatric patients, or for patients who have difficulty swallowing tablets. Processes for preparing the pharmaceutical composition are also described.

Clinical studies on topiramate have revealed previously unrecognized pharmacological properties which suggest that topiramate would be effective in lowering lipids in humans, particularly in overweight individuals. Furthermore, topiramate improves both symptoms and objective electrophysiological measurements of peripheral neuropathy while also lowering levels of total cholesterol, triglyceride, blood glucose, and blood pressure and promoting significant weight loss. Some aspects of the current invention provide a method of treating optic nerve degeneration comprising reducing optic nerve degeneration and/or inducing the growth of optic nerve fibers and/or stimulating functions of optic nerves.

SUMMARY OF THE INVENTION

Some aspects of the invention relate to a method for treating or preventing macular degeneration of a patient comprising administering a compound, such as topiramate, its analog or derivatives, with a dosage safely effective to suppress or terminate drusen (of dry AMD) and/or exudate (of wet AMD). A dosage of topiramate herein may consist one dose or multiple doses administered over time. In one embodiment, the step of administering the topiramate comprises topical administration on the eye.

Some aspects of the invention relate to a method for treating or preventing optic nerve degeneration of a patient comprising administering a compound, such as topiramate, its analog or derivatives, with a dosage safely effective to induce growth of optic nerve fibers. In one embodiment, the step of administering the topiramate comprises topical administration on the eye.

Some aspects of the invention relate to a method for treating optic nerve degeneration of a patient comprising administering a compound, such as topiramate, its analog or derivatives, with a dosage safely effective to induce growth of optic nerve fibers. In one embodiment, the step of administering the topiramate compound comprises topical administration on the eye. In another embodiment, the step of administering the topiramate compound comprises injection to an area at or adjacent to the optic nerve fibers in the eye.

Some aspects of the invention relate to a method for rejuvenating nerve fibers of a patient comprising administering a compound, such as topiramate, its analog or derivatives, with a dosage safely effective to induce growth of the nerve fibers.

In a further embodiment, the step of administering the topiramate is topical administration formulated in various dosage forms suitable for topical delivery, including solutions, suspensions, emulsions, and gels.

In a further embodiment, the therapeutically effective amount is from about 0.0001% to 5% by weight in the pharmaceutical composition, preferably from about 0.01% to 2% by weight in the pharmaceutical composition.

In a further embodiment, the compound or pharmaceutical composition is administered to a surface of the eye 1 to 4 times per day or per week. In one embodiment, the compound further comprises pharmaceutically acceptable buffers and pH adjusting agents, wherein the pharmaceutical composition is adjusted in the pH range of about 4 to 9.

Some aspects of the invention relate to a method for protecting optic nerve comprising, adjunctively administering at least one IOP (intraocular pressure) lowering agent and topiramate, in combination, in series, or simultaneously.

In a further embodiment, the IOP-lowering agent is selected from a group consisting of miotics, alpha and alpha/beta adrenergic agonists, beta-blockers, prostaglandins and their analogues and derivatives, and carbonic anhydrase inhibitors. In another embodiment, the IOP-lowering agent is selected from a group consisting of timolol, betaxolol, S-betaxolol levobunolol, carteolol, pilocarpine, carbachol, epinephrine, dipivalyl epinephrine-α methyl dipivalylepinephrine, brinzolamide, dorzolamide, unoprostone, latanoprost, travoprost, apraclonidine, brimonidine, acetylcholinesterase inhibitors, acetazolamide, methazolamide ethoxzolamide, triamcinolone acetonide, para-amino clonidine, muscarinic antagonists, and metabolite derivatives of arachindonic acid.

DETAILED DESCRIPTION OF EXEMPLARY EMBODIMENTS

The following detailed description is of the best presently contemplated modes of carrying out the invention. This description is not to be taken in a limiting sense, but is made merely for the purpose of illustrating general principles of embodiments of the invention.

Topiramate (an active ingredient in TOPAMAX® marketed by Ortho-McNeil Pharmaceutical, a Johnson & Johnson company, N.J., USA) is a sulfamate-substituted monosaccharide that is intended for use as an antiepileptic drug. It is available as 25 mg, 100 mg, and 200 mg round tablets for oral administration. Topiramate is a white crystalline powder with a bitter taste. Topiramate is most soluble in alkaline solutions containing sodium hydroxide or sodium phosphate and having a pH of 9 to 10. It is freely soluble in acetone, chloroform, dimethylsulfoxide, and ethanol. The solubility in water is 9.8 mg/mL. Its saturated solution has a pH of 6.3.

As used herein and unless otherwise indicated, the term "topiramate" refers to 2,3:4,5-Di-O-isopropylidene-β-D-fructopyranose sulfamate and isomers and mixtures of isomers thereof. Topiramate has the molecular formula $C_{12}H_{21}NO_8S$ and a molecular weight of 339.36. In particular, while "topiramate" conventionally refers to the specific compound named 2,3:4,5-Di-O-isopropylidene-β-D-fructopyranose sulfamate and represented by formula I, below, the term is used herein to refer to all enantiomerically and/or diastereomerically pure isomers of that specific compound, as well as mixtures of such isomers.

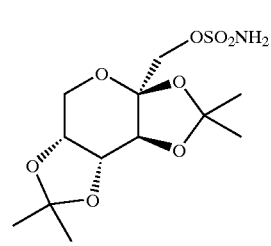

(Formula I)

Furthermore, the term "topiramate", as used herein unless otherwise indicated, encompasses sulfamic acid 2,2,7,7-tetramethyl-tetrahydro-bis[1,3]dioxolo[4,5-b, 4',5'-d]pyran-3a-ylmethyl ester, which is represented by formula II below and enantiomerically and/or diastereomerically pure forms thereof, as well as mixtures of such forms.

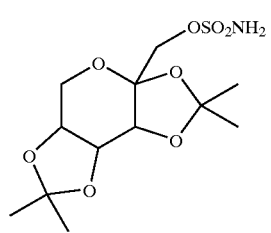

(Formula II)

TOPAMAX® (topiramate as an active ingredient) tablets contain the following inactive ingredients: lactose monohydrate, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide (100 and 200 mg tablets) and polysorbate 80. It is typically dosed twice daily. Some aspects of the invention relate to an eye-drop compound containing topiramate as an active ingredient with certain inactive ingredients as a form of solutions, suspensions, emulsions, and gels.

TOPAMAX® is one of the newly approved anti-epileptic drugs (AED) approved by the FDA in the last 10 years. It is considered a broad spectrum AED because it works to prevent both partial onset and generalized seizures. Topiramate has potentially five mechanisms of action. They include the blockage of sodium channels (similar to many of the traditional epileptics), enhancement of GABA-a receptors (an inhibitory neurotransmitter), inhibitory effect on glutamate receptors, inhibition of L-type high-voltage calcium ion channels, and a diamox type effect. The relatively importance of these mechanisms in the functioning of topiramate is not clearly known but it does not appear that any other single AED shares these five properties.

TOPAMAX® lacks many of the more serious side effects seen with the older AEDs including a lack of known problems with bone marrow and an extremely small incidence of liver abnormalities apparently confined to patients with prior liver abnormalities. It does have a fairly common side effect of kidney stones (between 1–2%). It is also one of only two AEDs that have a statistically proven propensity to lose weight. Other side effects include a change in taste, particularly with carbonated drinks, tingling in the extremities, and at times interference with mental function. The last side effect is highly dependent upon the rate of dose administration and is relatively uncommon among patients started at a low dose and advanced slowly. Dosing rates must be individualized based upon the patient and the other medications they are currently prescribed. Some aspects of the invention provide a method of inducing growth of new optic nerve fibers with topiramate either administered topically in a non-systemic, site-specific manner on the eye, intravitral injection, or injected to an area at or adjacent to the optic nerve fibers in the eye. The dosage for such non-systemic, site-specific administration is only a small fraction (usually, a hundreds or thousands) of the amount of topiramate used in conventional oral or systemic administration.

Among the most common uses of TOPAMAX® is the prevention of migraines. The medication works as well for prevention of migraines as it works well for 50% of the patients given the medication. If one increases the dose slowly, the medication seems to be well tolerated. The migraine patients are generally taking from 100–200 Mg/day in two divided doses.

As an AED, TOPAMAX® has been shown to be highly effective. Like all other AEDs studied in head to head trials, there is no AED which is more effective than any other AED when used as initial therapy for the correct seizure type. Topiramate's advantage over the older AEDs is the lack of some of their more serious side effects. Less commonly than some of the other AEDs, topiramate is used for neuropathic pain relief. In some groups of patients, diabetics for example, the potential of weight loss is desirable and may therefore be a major reason for trying this medication for the treatment of diabetic neuropathic pain. TOPAMAX® has been shown in open label trials to be useful for essential type tremor. It has been shown in multiple small trials to be effective in cluster headache.

Topiramate is a relatively new anticonvulsant drug with a fructopyranose-sulphamate chemical structure, which has been licensed for adjunctive therapy in patients with intractable partial epilepsy. It has recently been approved for expanded seizure indications, including adjunctive therapy in children with partial onset seizures and for monotherapy. Topiramate is rapidly and efficiently absorbed from the GI tract after which it is eliminated, predominantly unchanged, via the renal route with a plasma t½ of 20–30 hrs. However, a proportion of the drug undergoes hepatic metabolism by oxidative pathways and the clearance is increased by enzyme inducing drugs. Topiramate is only 15% protein bound, and is a weak carbonic anhydrase inhibitor and is thus also bound to a high affinity, low capacity binding site on erythrocytes. A reference range is established within which topiramate is likely to be effective without causing toxicity. Therapeutic drug monitoring is particularly useful when non-compliance or toxicity is suspected, but should also be applied when modifying treatment in any way or to establish baseline values during successful treatment.

U.S. Pat. No. 6,559,293, entire contents of which are incorporated herein by reference, discloses topiramate sodium trihydrate, and pharmaceutically acceptable polymorphs, solvates, hydrates, dehydrates, co-crystals, anhydrous, or amorphous forms thereof, as well as pharmaceutical compositions and pharmaceutical unit dosage forms containing the same. In particular, the patent discloses methods of treating or preventing a variety of diseases and conditions including seizures, epileptic conditions, tremors, cerebral function disorders, obesity, neuropathic pain, affective disorders, tobacco cessation, migraines, and cluster headache. Further, the prior art invention discloses methods of treating or preventing neuralgia, trigeminal neurologia, diabetic neuropathy and other forms of nerve damage, allodynia, paraesthesia, hyperaesthesia, phantom pain, phantom limb pain, hyperalgesia, and tinnitus. However, the invention does not disclose means for inducing or stimulating the growth pf new nerve fibers, particularly optic nerve fibers.

Any of the pain-alleviating anticonvulsants may be used herein for treating macular degeneration, for reducing optic nerve degeneration, or for inducing or stimulating the growth of new nerve fibers, particularly optic nerve fibers in a subject in need thereof comprising administering to the subject a therapeutically effective amount of anticonvulsant compounds, though the mechanism is not fully understood. For extensive listings of anticonvulsants, see, e.g., Goodman and Gilman's "The Pharmaceutical Basis Of Therapeutics", 8th ed., McGraw-Hill, Inc. (1990), pp. 436–462, and "Remington's Pharmaceutical Sciences", 17th ed., Mack Publishing Company (1985), pp. 1075–1083. Specific neuropathic pain-alleviating anticonvulsants that may be used herein include lamotrigine, gabapentin, valproic acid, topiramate, famotodine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan.

As used herein and unless otherwise indicated, the term "adjunctively administering" refers to the administration of one or more compounds or active ingredients in addition to a pharmaceutically acceptable topiramate, either simultaneously with the same or at intervals prior to, during, or following administration of the pharmaceutically acceptable topiramate to achieve the desired therapeutic or prophylactic effect.

The compositions can be administered alone or in combination with at least one other agent, such as stabilizing compounds, which can be administered in any sterile, biocompatible pharmaceutical carrier, including, but not limited to, saline, buffered saline, dextrose, and water. The compositions can be administered to a patient alone, or in combination with other agents, drugs, genes, growth factors, anti-angiogenesis agents, or hormones.

Macular and Optic Nerve Degeneration

The eye is often compared to a camera. The front of the eye contains a lens that focuses images on the back of the eye. This area, called the retina, is covered with special nerve cells that react to light, like film in a camera. These nerve cells are very close together in the middle of the retina where the eye focuses the images that we see. This part of the retina is called the macula. The macula comprises cone cells (about 7 millions in number) in this area responsible for producing sharp, detail vision and color vision. The light comes to the retina, where the rod cells are stimulated to set off a chain of split-second chemical reactions converting light to electrical impulses.

The optic nerve, or nerve of sight, consists mainly of fibers derived from the ganglionic cells of the retina. These axons terminate in arborizations around the cells in the lateral geniculate body, pulvinar, and superior colliculus which constitute the lower or primary visual centers. From the cells of the lateral geniculate body and the pulvinar fibers pass to the cortical visual center, situated in the cuneus and in the neighborhood of the calcarine fissure. A few fibers of the optic nerve, of small caliber, pass from the primary centers to the retina and are supposed to govern chemical changes in the retina and also the movements of some of its elements (pigment cells and cones). There are also a few fine fibers, afferent fibers, extending from the retina to the brain, that are supposed to be concerned in pupillary reflexes.

The optic nerve is peculiar in that its fibers and ganglion cells are probably third in the series of neurons from the receptors to the brain. Consequently the optic nerve corresponds rather to a tract of fibers within the brain than to the other cranial nerves. Its fibers pass backward and medialward through the orbit and optic foramen to the optic commissure where they partially decussate. The mixed fibers from the two nerves are continued in the optic tracts, the primary visual centers of the brain.

The orbital portion of the optic nerve is from 20 mm to 30 mm in length and has a slightly sinuous course to allow for movements of the eyeball. It is invested by an outer sheath of dura mater and an inner sheath from the arachnoid which are attached to the sclera around the area where the nerve fibers pierce the choroid and sclera of the bulb. A little behind the bulb of the eye the central artery of the retina with its accompanying vein perforates the optic nerve, and runs within it to the retina. As the nerve enters the optic foramen its dural sheath becomes continuous with that lining the orbit and the optic foramen. In the optic foramen the ophthalmic artery lies below and to its outer side. The intercranial portion of the optic nerve is about 10 mm in length. Some aspects of the invention relate to a method for preventing or treating optic nerve degeneration of a patient comprising administering topiramate topically with a dosage safely effective to induce growth of optic nerve fibers.

There are two types of age-related macular degeneration (AMD): the dry (atrophic) form and the wet (exudative) form. The dry form of AMD affects about 90 percent of AMD patients and usually begins with the formation of tiny yellow deposits called drusen in the macula. Drusen usually do not cause serious loss of vision, but can cause distortion of vision. However, for reasons that are not yet understood, sometimes drusen will cause the macula to thin and break down, slowly leading to vision loss. The wet form of AMD occurs in about 10 percent of AMD patients. It is caused by the growth of abnormal blood vessels beneath the macula that can leak fluid and blood to form exudate. The wet form of AMD typically causes significant vision problems in the affected eye and can progress very rapidly, causing permanent central vision loss.

The exact cause of AMD is not known. AMD may be hereditary. If someone in the family has or had AMD, other member of the family may be at higher risk for developing the disease. These conditions are called age-related macular degeneration. If there are no new blood vessels being created, it is "dry" macular degeneration. When new blood vessels start to grow, it is called "wet" macular degeneration.

The exact cause of macular degeneration has not been found. Things like smoking, exposure to direct sunlight over a period of years, a lack of vitamin A and some medical conditions seem to make people more likely to get macular degeneration. Some people also seem to inherit a tendency to have macular degeneration. None of these things can really be said to cause macular degeneration.

The doctor may notice some things during the examination, or the patient may mention symptoms, that could be caused by macular degeneration. The symptoms are: the ability to see fine details when one is looking directly at an object, no matter how close or far away it is, starts to decline, vision changes so that straight lines look wavy or broken, and dark spots, lines, or shadows appear across the middle of the field of view. When these symptoms are caused by macular degeneration, they can occur in just one eye or in both eyes. Usually, the problem is noticed first in one eye.

Macular degeneration may never get better on its own. When macular degeneration goes from the "dry" form with drusen to the "wet" form with exudate, there can be a permanent loss of vision. The wet or exudative form of AMD is caused by the growth of abnormal blood vessels at the back of the eye that can leak fluid and blood (characterized as exudate). The wet form of AMD typically causes significant vision problems in the affected eye and can progress very rapidly and cause permanent vision loss. In some aspects of the invention, it is provided a method for treating macular degeneration of a patient comprising administering topiramate with a dosage safely effective to suppress degeneration or induce growth of new optic nerve fibers. A dosage of topiramate herein may consist one dose or multiple doses administered over time, preferably topically.

Even if all of the structures of the eye work perfectly, what we know as vision cannot happen without the brain's interpretation of the electrical impulses sent by the retina. The optic nerve is the bundle of retinal fibers that exits the back of the eye and transports electrical impulses to the brain where they are interpreted in the primary visual cortex.

New blood vessel may grow on the optic nerve head and into the vitreous (the clear gel inside the eye). This condition is common in patients with proliferative diabetic retinopathy. In some aspects of the invention, it is provided a method for treating nerve degeneration of a patient comprising administering topiramate with a dosage safely effective to suppress nerve degeneration or induce growth of new nerve fibers. In one embodiment, the administration may be systemic, or non-systemic that is site specific.

Compound Composition

The topiramate, its analog, isomers, or derivatives (collectively or individually called "compound") can be incorporated into various types of ophthalmic formulations for topical delivery to the eye or injection to an area at or adjacent to the optic nerve fibers in the eye. They may be combined with ophthalmologically acceptable preservatives, surfactants, viscosity enhancers, penetration enhancers, buffers, sodium chloride, and water to form aqueous, sterile ophthalmic suspensions or solutions. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a thickener, such as, hydroxymethylcellulose, hydroxyethylcellulose, hydroxypropylmethylcellulose, methylcellulose, polyvinyl-pyrrolidone, or the like, to improve the retention of the formulation inside an eye. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated. Preparation of such topical formulations are well described in the art of pharmaceutical formulations as exemplified, for example, by Remington's Pharmaceutical Science, Edition 17, Mack Publishing Company, Easton, Pa.

When dosed topically, the compounds are preferably formulated as topical ophthalmic suspensions or solutions, with a pH of about 4 to 9, preferably about 7. The compounds will normally be contained in these formulations in an amount 0.0001% to 5% by weight, but preferably in an amount of 0.01% to 2% by weight. Thus, for topical presentation, 1 to 2 drops of these formulations would be delivered to the surface of the eye 1 to 4 times per day or per week according to the routine discretion of a skilled clinician.

The preferred compound, (topiramate, its analog, isomers, or derivatives) may be mixed with an IOP(intraocular pressure)-lowering agent for treating glaucoma patients. The IOP-lowering agents useful in the present invention include all presently known IOP-lowering pharmaceuticals, including, but not limited to, miotics (e.g., pilocarpine, carbachol, and acetylcholinesterase inhibitors); alpha and alpha/beta adrenergic agonists (e.g., epinephrine, dipivalylepinephrine, para-amino clonidine, and brimonidine); beta-blockers (e.g., betaxolol, S-betaxolol, levobunolol, carteolol, and timolol); prostaglandins and their analogues and derivatives, such as, compounds disclosed in U.S. Pat. No. 4,599,353; No. 5,093, 329; and No. 5,321,128; and carbonic anhydrase inhibitors (e.g., acetazolamide, methazolamide, and ethoxzolamide), and compounds disclosed in U.S. Pat. No. 5,153,192; No. 5,240,923; No. 5,378,703; and No. 4,797,413 and ocular hypertensive lipids, such as those compounds (neutral replacement of the carboxylic acid group of prostaglandin F2α e.g. AGN 192024) described in IOVS, Mar. 15, 1998, Vol. 39, No. 4; WO 97/30710, U.S. Pat. Nos. 5,238,961; 5,262,437; 5,328,933; 5,352,708; 5,312,842; 5,552,434; 5,545,665; and 5,688,819. All of the above-cited patents and literature are incorporated herein by reference in their entireties. The preferred IOP-lowering agents applicable in the present invention are: timolol, betaxolol, S-betaxolol levobunolol, carteolol, pilocarpine, carbachol, epinephrine, dipivalyl epinephrine-α methyl dipivalylepinephrine, brinzolamide, dorzolamide, unoprostone, latanoprost, travoprost, apraclonidine, brimonidine, acetylcholinesterase inhibitors, acetazolamide, methazolamide ethoxzolamide, triamcinolone acetonide, para-amino clonidine, muscarinic antagonists, and metabolite derivatives of arachindonic acid.

The topiramate compound with one or more IOP-lowering agents is administered topically at a concentration of between 0.0001 and 5.0 wt %, preferably, 0.01 to 2.5 wt %, but preferably 0.001–0.005 for prostaglandins. Some aspects of the invention relate to a method for protecting optic nerve comprising, adjunctively administering at least one IOP-lowering agent and topiramate, in combination, in series, or simultaneously.

In addition to topiramate compound, the additional ingredient(s) that can be included in the compositions of the present invention include all ophthalmic, dermatological, otic or nasal agents that can be topically applied or injected to an area at or adjacent to the optic nerve fibers in the eye. In one embodiment, IOP-lowering agent is added to the compound formulation to counteract any potential glaucoma effects of topiramate, if any. For example, such ophthalmic agents include (but are not limited to): anti-glaucoma agents, such as beta-blockers (e.g., betaxolol and timolol), muscarinics (e.g., pilocarpine), prostaglandins, carbonic anhydrase inhibitors (e.g., acetazolamide, methazolamide, and ethoxzolamide), dopaminergic agonists and antagonists, and alpha adrenergic receptor agonists, such as para-amino clonidine (also known as apraclonidine) and brimonidine; anti-infectives, such as ciprofloxacin; non-steroidal and steroidal anti-inflammatories, such as suprofen, ketorolac, dexamethasone, rimexolone and tetrahydrocortisol; proteins; genes; growth factors, such as EGF; anti-angiogenesis agents; and anti-allergic agents, such as cromolyn sodium, emedastine and olopatadine. Compositions of the present invention may also include combinations of active ingredients.

The compositions of the present invention can also include other components, for example, pharmaceutically acceptable buffers; tonicity agents; comfort-enhancing agents; solubilizing aids; pH adjusting agents; antioxidants; and stabilizing agents. The compositions may also contain additional preservatives. As will be appreciated by those skilled in the art, the compositions may be formulated in various dosage forms suitable for topical delivery, including solutions, suspensions, emulsions, and gels. In one embodiment, the compositions may be formulated in various dosage forms suitable for implantation with slow-release characteristics or injection to an area at or adjacent to the optic nerve fibers in the eye.

Some aspects of the invention relate to a method for treating macular degeneration in a subject in need thereof comprising administering to the subject a therapeutically effective amount of a compound of topiramate, its analogs, isomers, or derivatives thereof. Furthermore, some aspects of the invention relate to a method for treating optic nerve degeneration in a mammal comprising administering to such a mammal a therapeutically effective amount for treating such condition of a compound of topiramate, its analogs, isomers, or derivatives thereof. The term "treating" is herein intended to mean treating, preventing unfavorable effects, managing, or stimulating favorable effects with respect to the diseases or symptoms.

From the foregoing description, it should now be appreciated that a novel method for treating or preventing macular and/or optic nerve degeneration comprising administering topiramate with a dosage effective to suppress degeneration or induce growth of new optic nerve fibers is disclosed. While the invention has been described with reference to a specific embodiment, the description is illustrative of the invention and is not to be construed as limiting the invention. Various modifications and applications may occur to those who are skilled in the art, without departing from the true spirit and scope of the invention.

What is claimed is:

1. A method for treating macular degeneration in a subject in need thereof comprising administering to the subject a therapeutically effective amount of a compound of topiramate, its analogs, isomers, or derivatives thereof.

2. The method of claim 1, wherein the compound is administered as a topical pharmaceutical composition onto an eye.

3. The method of claim 2, wherein the therapeutically effective amount is from about 0.0001% to 5% by weight in said pharmaceutical composition.

4. The method of claim 2, wherein the therapeutically effective amount is from about 0.01% to 2% by weight in said pharmaceutical composition.

5. The method of claim 2, wherein the compound is administered to a surface of the eye 1 to 4 times per day or per week.

6. The method of claim 2, wherein the compound further comprises pharmaceutically acceptable buffers and pH adjusting agents.

7. The method of claim 6, wherein the pharmaceutical composition is adjusted in the pH range of about 4 to 9.

8. The method of claim 1, wherein the pharmaceutical composition further comprises a second active ingredient of IOP-lowering agent.

9. The method of claim 8, wherein the IOP-lowering agent is selected from a group consisting of miotics, alpha and alpha/beta adrenergic agonists, beta-blockers, prostaglandins and their analogues and derivatives, and carbonic anhydrase inhibitors.

10. The method of claim 8, wherein the IOP-lowering agent is selected from a group consisting of timolol, betaxolol, S-betaxolol levobunolol, carteolol, pilocarpine, carbachol, epinephrine, dipivalyl epinephrine-α methyl dipivalylepinephrine, brinzolamide, dorzolamide, unoprostone, latanoprost, travoprost, apraclonidine, brimonidine, acetylcholinesterase inhibitors, acetazolamide, methazolamide ethoxzolamide, triamcinolone acetonide, para-amino clonidine, muscarinic antagonists, and metabolite derivatives of arachindonic acid.

11. The method of claim 1, wherein the step of administering is carried out by formulating the compound in various dosage forms suitable for implantation with slow-release characteristics.

12. The method of claim 2, wherein the compound further comprises ophthalmologically acceptable substance selected from a group consisting of preservatives, surfactants, viscosity enhancers, penetration enhancers, buffers, sodium chloride, water, and combination thereof.

13. The method of claim 2, wherein the compound further comprises a thickener selected from a group consisting of hydroxymethylcellulose, hydroxyethylcellulose, hydroxypropylmethylcellulose, methylcellulose, polyvinyl-pyrrolidone, and combination of.

14. The method of claim 2, wherein the topical pharmaceutical composition is configured in a formulation selected from a group consisting of solution, gel, suspension, emulsion, and ointment.

15. The method of claim 2, wherein the compound further comprises pharmaceutically acceptable substance selected from a group consisting of tonicity agents, comfort-enhancing agents, solubilizing aids, antioxidants and stabilizing agents.

* * * * *